United States Patent [19]

Murai et al.

[11] Patent Number: 5,476,869
[45] Date of Patent: Dec. 19, 1995

[54] INSECTICIDAL AND ACARICIDAL COMPOSITION

[75] Inventors: Keizaburo Murai, Naruto; Satoshi Nakamura, Kakogawa, both of Japan

[73] Assignees: Sumitomo Chemical Company, Limited; Otsuka Chemical Company, Ltd., both of Osaka, Japan

[21] Appl. No.: 244,724

[22] PCT Filed: Oct. 8, 1993

[86] PCT No.: PCT/JP93/01454

§ 371 Date: Jun. 17, 1994

§ 102(e) Date: Jun. 17, 1994

[87] PCT Pub. No.: WO94/08457

PCT Pub. Date: Apr. 28, 1994

[30] Foreign Application Priority Data

Oct. 19, 1992 [JP] Japan ................................. 4-279923

[51] Int. Cl.$^6$ .......................... A01N 37/34; A01N 37/52; A01N 47/16
[52] U.S. Cl. .......................... 514/477; 514/508; 514/521
[58] Field of Search .................................. 514/508, 521, 514/477

[56] References Cited

U.S. PATENT DOCUMENTS

| | | | |
|---|---|---|---|
| 4,297,370 | 10/1981 | Soboczenski | 424/298 |
| 4,444,786 | 4/1984 | Goto et al. | 424/248 |
| 5,120,721 | 6/1992 | Morimoto et al. | |

FOREIGN PATENT DOCUMENTS 0008474  3/1980  European Pat. Off. .

OTHER PUBLICATIONS

Worthing et al, The Pesticide Manual, 9th Ed. (1991) pp. 15 & 377.

*Primary Examiner*—Allen J. Robinson
*Attorney, Agent, or Firm*—Stevens, Davis, Miller & Mosher

[57] ABSTRACT

An insecticidal and acaricidal composition comprising, as active ingredients, (a) α-cyano-3-phenoxybenzyl 2,2,3,3-tetramethylcyclopropanecarboxylate and (b) ethyl (Z)—H-benzyl-N-[{methyl(1-methylthioethylideneamino-oxycarbonyl)amino} thio]-β-alaninate, and a method of controlling insects and acarines by applying said composition to sites where insects and acarines inhabit.

7 Claims, No Drawings

INSECTICIDAL AND ACARICIDAL COMPOSITION

This application is a 371 of PCT/JP93/01454, filed Oct. 8, 1993.

The present invention is intended to provide an insecticidal and acaricidal composition having excellent insecticidal and acaricidal activities.

The present inventors made study in order to develop an excellent insecticidal and acaricidal agent and, as a result, found that the composition shown below exhibits striking insecticidal and acaricidal effects by the synergistic actions of the active ingredients contained therein. The finding has led to the completion of the present invention. The present invention provides an insecticidal and acaricidal composition comprising, as active ingredients, α-cyano-3-phenoxybenzyl 2,2,3,3-tetramethylcyclopropanecarboxylate (hereinafter referred to as "compound 1") and ethyl (Z)—N-benzyl-N-[{methyl(1-methylthioethylideneamino-oxycarbonyl)amino} thio]-β-alaninate (commonly called "alanycarb" and hereinafter referred to as "compound 2").

There are shown below the structural formulas of the compound 1 and the compound 2, which are both the active ingredients of the insecticidal and acaricidal composition according to the present invention (hereinafter referred to as the present invention composition).

TABLE 1

| Compound | Chemical structure |
|---|---|
| Compound 1 | (structural formula of α-cyano-3-phenoxybenzyl 2,2,3,3-tetramethylcyclopropanecarboxylate) |
| Compound 2 | (structural formula of alanycarb) |

The compound 1 includes stereoisomers. The compound 1 used in the present invention includes any isomers having insecticidal activities and mixtures thereof.

The compound 1 includes, for example, the following compounds.

(RS)-α-cyano-3-phenoxybenzyl 2,2,3,3-tetramethylcyclopropanecarboxylate (commonly called fenpropathrin, hereinafter referred to as "compound 1-a") (S)-α-cyano-3-phenoxybenzyl 2,2,3,3-tetramethylcyclopropanecarboxylate The compound 2 can be produced by the process described in U.S. Pat. No. 4444786.

The injurious insects and acarines which can be controlled or exterminated by the present invention composition, include, for example, the followings.

THYSANOPTERA

*Scirtothrips dorsalis* (yellow tea thrips), *Frankliniella intonsa* (flower thrips) and the like.

HEMIPTERA

Aphids such as *Myzus persicae* (green peach aphid), *Myzus varians*, *Myzus mumecola*, *Schizaphis piricola*, *Aphis citricola* (spiraea aphid), *Aphis qossypii* (cotton aphid) and the like.

Mealybugs such as *Planococcus kraunhiae* (Japanese mealybug), *Pseudococcus comstocki* (Comstock mealybug) and the like.

Scales such as *Unaspis yanonensis* (arrowhead scale) and the like.

Whiteflies such as *Trialeurodes aporariorum* (greenhouse whitefly), *Bemisia tabaci* (sweetpotato whitefly) and the like.

Lace bugs such as *Stephanitis nashi* (pear lace bug), *Sephanitis pyrioides* (azalea lace bug) and the like.

Leafhoppers such as *Nephotettix cincticeps* (green rice leafhopper), *Arboridia apicalis* (grape leafhopper) and the like.

Planthoppers such as *Nilaparvata lugens* (brown rice planthopper), *Sogatella furcifera* (whitebacked rice planthopper), *Laodelphax striatellus* (small brown planthopper) and the like.

LEPIDOPTERA

Fruit moths such as *Grapholita molesta* (oriental fruit moth), *Carposina niponensis* (peach fruit moth) and the like.

Leafroller moths such as *Adoxophyes* sp. (smaller tea tortrix), *Adoxophyes orana fasciata* (summer fruit tortrix), *Archips fuscocupreanus* (apple tortrix) and the like.

*Conoqethes punctiferalis* (peach moth), *Spodoptera litura* (common cutworm), *Spodoptera exigua* (beet armyworm), *Ostrinia furnacalis* (oriental corn borer), *Pseudaletia separata* (rice armyworm), *Helicoverpa assulta* (oriental tobacco budworm), *Leguminivora glycinivorella* (soybean pod borer), *Phyllonorycter ringoniella* (apple leafminer), *Lyonetia prunifoliella malinella*, *Lyonetia clerkella* (peach leafminer), *Phyllocnistis citrella* (citrus leafminer), *Mamestra brassicae* (cabbage armworm), *Autorpha nigrisigna* (beet semi-looper), *Hyphantria cunea* (fall webworm), *Pieris rapae crucivora* (common cabbage worm) and the like.

COLEOPTERA

*Epilachna vigntioctopunctata* (twenty-eight-spotted ladybird), *Anomala cupre* (cupreous chafer), *Anoplophora malasiaca* (white spotted longicorn beetle), *Xylotrechus pyrrhoderus* (grape borer) and the like.

DIPTERA

*Delia platura* (seedcorn maggot), *Liriomyza chinensis* (stone leek leafminer) and the like.

TYLENCHIDA

Nematodes such as *Meloidogyne incognita* (southern root-knot nematode), *Meloidogyne hapla* (northern root-knot nematode), *Pratylenchus penetrans* (Cobb root-lesion nematode) and the like.

ACARINA

Spider mites such as *Tetranychus urticae* (two-spotted spider mite), *Tetranychus cinnabarinus* (carmine spider mite), *Tetranychus kanzawai* (Kanzawa spider mite), *Panonychus ulmi* (European red mite), *Panonychus citri* (citrus red mite) and the like.

The method for formulating the present invention composition and the method for applying the composition are hereinafter described specifically.

In formulating the present invention composition, there are mixed, by an ordinary method, the active ingredients according to the present invention, appropriate carriers and auxiliary substances such as surfactant, binder, stabilizer and the like to obtain a wettable powder, an emulsifiable concentrate, a flowable, a dust, a DL dust, etc. In this case, the mixing ratio of the compound 1 and the compound 2 is ordinarily 1:1 to 1:50 by weight, preferably 1:2 to 1:10 by weight, and the total content of the active ingredients in the composition is ordinarily 1–80% by weight.

The carriers usable in the present invention composition can be any solid or liquid carrier commonly used in agricultural or horticultural chemicals, and is not restricted to any particular carrier.

The solid carrier includes, for example, mineral powders, plant powders, alumina, silicates, polysaccharides and waxes.

The liquid carrier includes, for example, water, alcohols, aromatic hydrocarbons, halogenated hydrocarbons, ethers, ketones, esters, nitriles, alcohol ethers, aliphatic or alicyclic hydrocarbons, industrial gasoline and petroleum fractions.

In producing a wettable powder, an emulsifiable concentrate, a flowable or the like, a surfactant, an emulsifier and the like are further used for the purposes of emulsification, dispersion, solubilization, wetting, foaming, spreading, etc. There may be further added, as necessary, stabilizers such as antioxidant, ultraviolet absorber and the like in appropriate amounts.

The present invention composition may be used in admixture with other acaricide, insecticide, attractant, repellent, fungicide, plant growth regulator, fertilizer, etc. Such mixed use enables expanded applications in, for example, target diseases and insects, application methods and application timings.

The present invention composition is used as follows. The dosage applied differs depending upon the size of each fruit tree or each vegetable to be treated, but is ordinarily 10–200 grams per 10 ares in terms of the total amount of active ingredients. In spraying the present invention composition, when the composition is a wettable powder or an emulsifiable concentrate, it is diluted with water and the diluted liquid is applied to fruit trees or vegetables ordinarily in an amount of 50–500 liters per 10 ares at a timing when pest insects occur.

The present invention is hereinafter described by way of Formulation Examples and Application Examples. However, the present invention is in no way restricted to these Examples alone. In the Examples, parts refer to parts by weight in all cases.

FORMULATION EXAMPLE 1

5 parts of the compound 1-a, 30 parts of the compound 2, 5 parts of sodium lauryl sulfate, 2 parts of a sodium nephthalenesulfonate-formalin condensate, 20 parts of white carbon and 33 parts of clay were ground and mixed uniformly to obtain a wettable powder.

FORMULATION EXAMPLE 2

5 parts of the compound 1-a, 30 parts of the compound 2, 15 parts of Sorpol 2564 (a mixed emulsifier consisting of nonionic and anionic surfactants, manufactured by Toho Kagaku) and 65 parts of xylol were mixed to obtain an emulsifiable concentrate.

The compound 1-a and the compound 2 are mixed at a weight ratio of 1:1, 1:2, 1:10 or 1:50 in the same manner as in Formulation Example 1 or 2, whereby various wettable powders or emulsifiable concentrates can be obtained.

APPLICATION EXAMPLE 1

A spray solution prepared by diluting of the wettable powder prepared in Formulation Example 1 to a given dilution ratio was sprayed onto young fruits of apple (variety: Fuji) in an amount of 50 milliliters per 3 fruits, using a spray gun equipped with a compressor. The young apple fruits were then air-dried, placed in same plastic cups (3 fruits per cup), and stored. One day thereafter, 10 adults of *Carposina niponensis* (peach fruit moth) were released into each cup and, 24 hours thereafter, the numbers of the alive and dead insects were examined to calculate an insect mortality (%). In this test, three fruits were used for each treatment in three replications.

The results are shown in Table 2.

TABLE 2

| Active ingredient(s) | Concentration(s) (ppm) | Insect mortality (%) |
|---|---|---|
| Compound 2 + compound 1-a | 300 + 50 | 100 |
| | 150 + 25 | 100 |
| | 75 + 12.5 | 97 |
| Compound 2 | 300 | 63 |
| | 150 | 13 |
| | 75 | 0 |
| Compound 1-a | 50 | 60 |
| | 25 | 30 |
| | 12.5 | 7 |
| Untreated | — | 0 |

APPLICATION EXAMPLE 2

A spray solution prepared by diluting the wettable powder prepared in Formulation Example 1 to a given dilution ratio was sprayed onto apple (variety: Fuji) fruits in a sufficient amount using a spray gun equipped with a compressor. One apple fruit was then stored in a thermostat chamber. 11 days after the spraying, 10 1st-instar larvae of *Carposina niponensis* (peach fruit moth) were released into the chamber. Three days thereafter, the number of entrance holes was examined for each apple fruit and the controlling effect was calculated using the following formula.

controlling effect (%)=[1—(total entrance holes of treated fruits)/ (total entrance holes of untreated fruits)]×100

In this test, one fruit was used for each treatment in three replications. The results are shown in Table 3.

TABLE 3

| Active ingredient(s) | Concentration(s) (ppm) | Controlling effect (%) |
|---|---|---|
| Compound 1-a + compound 2 | 50 + 300 | 100 |
| Compound 1-a | 100 | 23 |
| Compound 2 | 400 | 0 |
| Untreated | — | 0 |

APPLICATION EXAMPLE 3

A spray solution prepared by diluting of the wettable powder prepared in Formulation Example 1 to a given dilution ratio was sprayed onto apple (variety: Fuji) fruits in a sufficient amount using a spray gun equipped with a compressor. Thus treated fruits were then stored in a thermostat chamber of 25° C. 3 days thereafter, 10 4th-instar larvae of *Adoxophyes* sp. (smaller tea tortrix) were released into the chamber and, 1 day thereafter, the numbers of alive and dead larvae were examined to calculate an insect mortality (%). In this test, one fruit was used for each treatment in three replications. The results are shown in Table 4.

TABLE 4

| Active ingredient(s) | Concentration(s) (ppm) | Insect mortality (%) |
| --- | --- | --- |
| Compound 1-a + compound 2 | 50 + 300 | 72.0 |
| Untreated | — | 0 |

APPLICATION EXAMPLE 4

A spray solution prepared by diluting the wettable powder prepared in Formulation Example 1 to a given dilution ratio was sprayed onto peach trees (10-year old) (variety: Ohkubo) in a peach garden infested by *Grapholita molesta* (oriental fruit moth), in an amount of 6 liters per tree using a power sprayer. Three weeks thereafter, 95 to 230 shoots per tree were arbitrarily selected to examine the number of shoots damaged and the controlling effect (%) was calculated using the following formula. In this test, one tree was used for each treatment in two replications.

Controlling effect (%)=[1—(number of damaged shoots in treated tree)/(number of damaged shoots in untreated tree)]×100

The results are shown in Table 5.

TABLE 5

| Active ingredient(s) | Concentration(s) (ppm) | Controlling effect (%) |
| --- | --- | --- |
| Compound 1-a + compound 2 | 50 + 300 | 83.5 |
| Chlorpyrifos (commercial agent) | 250 | 55.1 |
| Untreated | — | 0 |

APPLICATION EXAMPLE 5

A spray solution prepared by diluting the wettable powder prepared in Formulation Example 1 to a given dilution ratio was sprayed onto peach trees (10-year old) (variety: Ohkubo) in a peach garden infested by *Conogethes punctiferalis* (peach moth), in an amount of 6 liters per tree using a power sprayer. 4 weeks thereafter, 18–151 fruits per tree were arbitrarily selected and the number of fruits damaged was examined. The controlling effect (%) was calculated using the following formula. In this test, one tree was used for each treatment in two replications.

Controlling effect (%)=[1—(number of damaged fruits in treated trees)/(number of damaged fruits in untreated trees)]×100

The results are shown in Table 6.

TABLE 6

| Active ingredient(s) | Concentration(s) (ppm) | Controlling effect (%) |
| --- | --- | --- |
| Compound 1-a + compound 2 | 50 + 300 | 77.2 |
| Chlorpyrifos (commercial agent) | 250 | 17.8 |
| Untreated | — | 0 |

APPLICATION EXAMPLE 6

A spray solution prepared by diluting the wettable powder prepared in Formulation Example 1 to a given dilution ratio was sprayed onto pear trees (10-year old) (variety: Nijusseiki) in a pear garden infested by *Schizaphis piricola*, in an amount of 4 liters per tree using a power sprayer. 3 days and 10 days thereafter, 10 shoots (each having 3 leaves) per tree were arbitrarily selected to examine the number of aphids on them. In this test, one tree was used for each treatment in three replications.

The results are shown in Table 7.

TABLE 7

| Active ingredient(s) | Concentration(s) (ppm) | Number of aphids/ 100 leaves | | |
| --- | --- | --- | --- | --- |
| | | 0* | 3* | 10* |
| Compound 1-a + compound 2 | 50 + 300 | 2073 | 1 | 21 |
| Carbaryl (commercial agent) | 850 | 2257 | 4 | 62 |
| Untreated | — | 1608 | 2286 | 1499 |

*days after treatment

APPLICATION EXAMPLE 7

Kidney bean leaves infested by *Tetranychus kanzawai* (Kanzawa spider mite) were cut off and dipped, for 10 seconds, in an aqueous solution prepared by diluting the wettable powder prepared in Formulation Example 1 to a given dilution ratio. After the dipping, one leaf was each placed in a cup and, 2 days after the dipping, a mite mortality was examined. In this test, one cup was used for each treatment in three replications. The results are shown in Table 8.

TABLE 8

| Active ingredient(s) | Concentration(s) (ppm) | Mite mortality (%) |
| --- | --- | --- |
| Compound 1-a + compound 2 | 50 + 300 | 92.1 |
| Untreated | — | 0 |

APPLICATION EXAMPLE 8

A spray solution prepared by diluting the wettable powder prepared in Formulation Example 1 to a given dilution ratio was sprayed onto young seedlings of cabbage in a greenhouse, in an sufficient amount using a small sprayer for home use. The young seeldings were then air-dried. 7 days and 13 days thereafter, the leaves were cut off and one leaf was placed in a cup. 10 3rd-instar larvae of *Spodoptera litura* (common cutworm) were released into the cup. 2 days after the release, the mortality of the insects was examined. In this test, one cup was used for each treatment in three replications. The results are shown in Table 9.

TABLE 9

| Active ingredient(s) | Concentration(s) (ppm) | Insect mortality (%) | | |
| --- | --- | --- | --- | --- |
| | | 0* | 7* | 13* |
| Compound 1-a + compound 2 | 50 + 300 | 100 | 100 | 97 |
| Untreated | — | 0 | 3 | 3 |

*days after treatment

We claim:

1. An synergistic insecticidal and acaricidal composition comprising, as active ingredients,
   (a) α-cyano-3-phenoxybenzyl 2,2,3,3-tetra-methylcyclopropanecarboxylate and
   (b) ethyl (Z)—N-benzyl-N-[{methyl(1-methylthioethylideneamino-oxycarbonyl)amino}thio]-β-alaninate in synergistic insecticidally, acaricidally, or both effective amount and further comprising agriculturally, horticulturally, or both acceptable carriers, wherein the weight ratio of (a) and (b) is 1:1 to 1:10.

2. The insecticidal and acaricidal composition according to claim 1, wherein the weight ratio of (a) and (b) is 1:2 to 1:10.

3. The insecticidal and acaricidal composition according to claim 1, wherein the weight ratio of (a) and (b) is about 1:6.

4. The insecticidal and acaricidal composition according to claim 1, wherein the total content of the active ingredients is 1–80%.

5. A method for controlling insects and acarines which comprises applying an effective amount of the synergistic insecticidal and acaricidal composition of claim 1 to sites where insects, acarines, or both inhabit.

6. The method for controlling insects and acarines according to claim 5, wherein the insecticidal and acaricidal composition is applied in an amount of 10–200 g per 10 ares in terms of the total amount of the active ingredients.

7. The method according to claim 6, wherein said insects are Hemiptera or Lepodoptera and said acarines are Acarina.

* * * * *